United States Patent [19]

Borden et al.

[11] Patent Number: 5,534,706
[45] Date of Patent: Jul. 9, 1996

[54] PARTICLE MONITOR FOR THROTTLED PUMPING SYSTEMS

[75] Inventors: Peter G. Borden, San Mateo; Derek G. Aqui, San Jose, both of Calif.; Matt A. Evanko, Placitas, N.M.

[73] Assignee: High Yield Technology, Inc., Sunnyvale, Calif.

[21] Appl. No.: 207,329

[22] Filed: Mar. 7, 1994

[51] Int. Cl.⁶ ............................. G01N 15/06; G01N 21/00
[52] U.S. Cl. ............................................. 250/574; 356/338
[58] Field of Search ............................. 250/573, 574, 250/575, 576; 356/337, 338, 341, 342, 244, 246

[56] References Cited

U.S. PATENT DOCUMENTS

| Re. 33,213 | 5/1990 | Borden et al. | 250/574 |
|---|---|---|---|
| 4,804,853 | 2/1989 | Borden et al. | 250/574 |
| 4,942,305 | 7/1990 | Sommer | 250/574 |
| 5,055,698 | 10/1991 | Borden | 250/574 |
| 5,083,865 | 1/1992 | Kinney et al. | 356/338 |
| 5,132,548 | 7/1992 | Borden et al. | 250/574 |
| 5,247,188 | 9/1993 | Borden | 250/574 |
| 5,266,798 | 11/1993 | Borden et al. | 250/239 |
| 5,360,980 | 11/1994 | Borden et al. | 250/573 |

OTHER PUBLICATIONS

Article entitled "High–Vacuum Technology" by Marsbed H. Hablanian, Marcel Dekker; New York, 1990, pp. 235–237.

*Primary Examiner*—Stephone Allen
*Attorney, Agent, or Firm*—Skjerven, Morrill, MacPherson, Franklin & Friel; Edward C. Kwok

[57] ABSTRACT

A method for accomplishing particle monitoring above the throttle valve of a turbo pump provides a particle sensor which is built into the throttle valve in such a way that it is insensitive to local plasma glows. Furthermore, the particle sensor is placed such that a particle monitoring laser beam of the particle sensor is offset from the centerline of the pipe, so as to maximize exposure to process gas flow which is diverted to the periphery of the pipe by the position of a butterfly valve plate.

12 Claims, 2 Drawing Sheets

PARTICLE MONITOR FOR THROTTLED PUMPING SYSTEMS

BACKGROUND OF THE INVENTION

1. Field of the Invention

The present invention relates to the design and placement of particle monitors in a manufacturing environment; and, in particular, relates to the design and placement of particle monitors in a low pressure chamber used in semiconductor processing, such as a plasma etch chamber.

2. Discussion of the Related Art

In semiconductor wafer processing, particle contamination in vacuum processing equipment (called "process tools") is one of the most common sources of yield loss. Consequently, particle monitors for detecting the levels of particles present in a process chamber during processing are developed.

One common technique for monitoring particles in a process chamber places a laser-based particle monitor in the exhaust line of a process tool. In such a laser-based monitor, exhaust gas from the process chamber passes through the particle monitor, carrying in it particles which are detected by laser light scattering. Laser-light scattering occurs in such a particle monitor when a particle passing through the beam scatters light to photocells of the particle monitor. The photocells create an electrical pulse indicating the presence of the particle when the scattered light is received. The use of laser-based sensors and techniques have been described, for example, in: (i) U.S. Pat. No. 4,804,853 to P. Borden et al, entitled "Compact Particle Flux Monitor", Ser. No. 07/041,795, filed on Apr. 23, 1987 and issued on Feb. 14, 1989 as U.S. Pat. No. 4,804,853; (ii) Reissued U.S. Pat. No. Re.33,213, reissued on May 8, 1990, which is based on U.S. Pat. No. 4,739,177 to P. Borden, entitled "Light Scattering Particle Detector for Wafer Processing Equipment", filed on Sep. 16, 1986, and issued on Apr. 19, 1988; (iii) and U.S. Pat. Nos. 5,132,548 and 5,266,798 to P. Borden et al, each entitled "High Sensitivity, Large Detection Area Particle Sensor for Vacuum Applications", having Ser. Nos. 07/582,718 and 07/742,798, issued on Jul. 21, 1992 as U.S. Pat. No. 5,132,548 and Nov. 30, 1993 as U.S. Pat. No. 5,266,798, and filed on Sep. 14, 1990 and Aug. 8, 1991, respectively. In addition, further discussion of laser-based particle monitoring techniques can be found in PG Borden, 10 part series in Microcontamination Magazine, January, February, March, April, May, August, September, October, November, and December issues, 1991.

However, there are some applications in which the use of particle monitors is impractical in the prior art. One such application is found in a low pressure plasma equipment, such as a plasma etcher, in which a turbo pump is used to maintain the reduced pressure required for the plasma etching operation. A turbo pump, which is in principle similar to a propeller, uses a rapidly spinning rotor with numerous blades to create a flow of exhaust gases from the process chamber. Such a pump is described in, for example, High-Vacuum Technology, by Marsbed H. Hablanian, Marcel Dekker, New York (1990), §7.2, pp. 235–237.

FIG. 1 shows a typical pumping configuration 100 of a plasma etcher for processing one or more semiconductor wafers within its process chamber. As shown in FIG. 1, process chamber 101 includes multiple electrodes (not shown) that are used to maintain a p:Lasma. During operation, a process gas is admitted through numerous fine holes in one of the electrodes, which is typically called the "shower head". Inside process chamber 101, the plasma created by the electrodes and the remaining gas flow uniformly bathe the exposed surfaces of the semiconductor wafers to allow the chemical reactions in a processing step, such as the etching a dielectric film, to occur. The exhaust gases of the chemical reactions are drawn out by a turbo pump 150. A normal mechanical pump (not shown) is connected to turbo pump 150 by pipe 151 to finally draw the gasses to atmospheric pressure.

In configuration 100, a butterfly valve 120 is typically used to maintain the pressure in process chamber 100. Butterfly valve 120 includes a circular plate 102 mounted on a drive shaft 103, which is driven by a motor 104. The entire assembly of butterfly valve 120, including a pump line 105 which houses butterfly valve 120, is also called a weldment. In butterfly valve 120, the variable positions of plate 102 allows a variable restriction of the opening above turbo pump 150. The amount of restriction varies with the angle of plate 102. For example, if the plane of plate 102 is normal to the axis of pump line 105, the restriction is maximum, and the gas flow is substantially entirely blocked. However, if the axis of pump line 105 lies in the plane of plate 102, the gas flow from the process chamber is substantially unblocked. Of course, intermediate angles of plate 102 provide different levels of restriction, Typically, the angle of plate 102 is controlled by a feedback loop, which includes a pressure sensor inside process chamber 101, to provide a stable pressure in process chamber 101. Alternatively, instead of butterfly valve 120, pressure control can also be achieved using a linear gate valve. A linear gate valve consists of a flat plate that slides across the opening of the pump line. Similar to butterfly valve 120, the position of the flat gate in a linear gate valve determines the restriction of the pump line. Thus, further description of a linear gate valve is omitted.

Ideally, particle monitoring should be carried out in the portion of the exhaust gas flow between the process chamber 101 and turbo pump 150, a region referred to as "above the pump". However, particle monitoring is not performed above the pump in the prior art because of the difficulties which are further described below. Instead, particle monitoring is typically performed "after the pump", i.e., downstream from turbo pump 150. For example, in FIG. 1, a particle monitor 152 is shown to be installed in pipe 151. However, after the pump particle monitoring is less desirable because the pumping action of turbo pump 150 provides a large amount of gas mixing. Gas mixing results from gas physically striking either the blades of turbo pump 150 or the boundary layer at the blade surfaces. Consequently, downstream chemical reactions can occur inside turbo pump 150, and particles may be removed or added to the gas flow by the blades and the pump bearings.

However, particle monitoring above the pump is not performed in the prior art for various reasons. First, the throat of turbo pump 150 is typically as close to process chamber 101 as possible, the region between turbo pump 150 and process chamber 100 is bathed with a strong glow from the plasma. The strong glow would swamp out the weaker intensity of any scattered light which is used by a dark field sensor to monitor particles. Second, the gas velocity in the region between process chamber 100 and turbo pump 150 is relatively high because of the low process pressure. In this region, velocities in the range of 10–20 m/sec are common. Particles at this velocity are not efficiently monitored by a dark field sensor, which typically has a maximum sensitivity range at lower particle velocities. Third, the region between turbo pump 150 and process chamber 101 does not provide adequate space for installing a dark field sensor, which includes at least a laser source, large area pick-up lens, and beam stop.

SUMMARY OF THE INVENTION

In accordance with the present invention an apparatus and a method are provided for monitoring particles in an exhaust line of a process chamber. The present invention is applicable to an exhaust line of the process chamber which is equipped with a throttle valve for restricting an opening of said exhaust line. The method of the present invention includes the steps of: (i) positioning a laser beam such that the laser beam crosses an opening created by said throttle valve, when the throttle valve is partially open; and (ii) positioning a detector for detecting particles impinged by said laser beam. In one embodiment, the laser beam is positioned offset from a principal axis of the exhaust line.

In one embodiment:, the laser beam of the present invention is provided by a bright-field particle sensor. In another embodiment, a detector is positioned to collect scattered light. Further, a narrow band optical filter can also be provided for attenuating noise due to the plasma glow in the process chamber. The throttle valve of the present invention can be implemented by one of numerous types of throttle valves, such as a butterfly valve or a linear gate valve.

The present invention is better understood upon consideration of the detailed description below and the accompanying drawings.

DETAILED DESCRIPTION OF PREFERRED EMBODIMENTS

The present invention is applicable to provide effective particle monitoring above a turbo pump, even in the presence of a plasma glow. To achieve this goal, the present invention configures a sensor to be relatively insensitive to plasma glows, and takes advantage that, under typical operating conditions, a butterfly valve is only slightly open. When the butterfly valve is only slightly open, most of the process gas flows and, hence, particles, are channelled through a relatively narrow opening.

Figure 1:
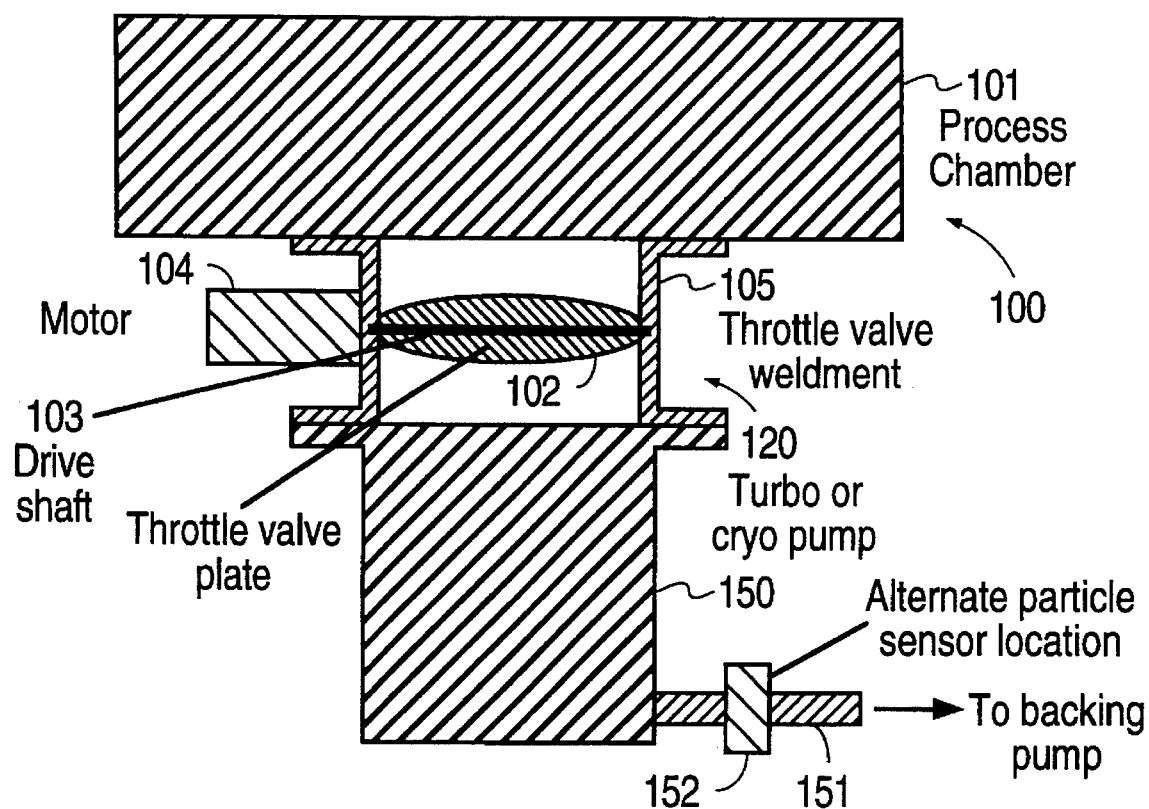
FIG. 1 shows a pumping configuration 100 of a typical low pressure process chamber 101.
Figure 2:
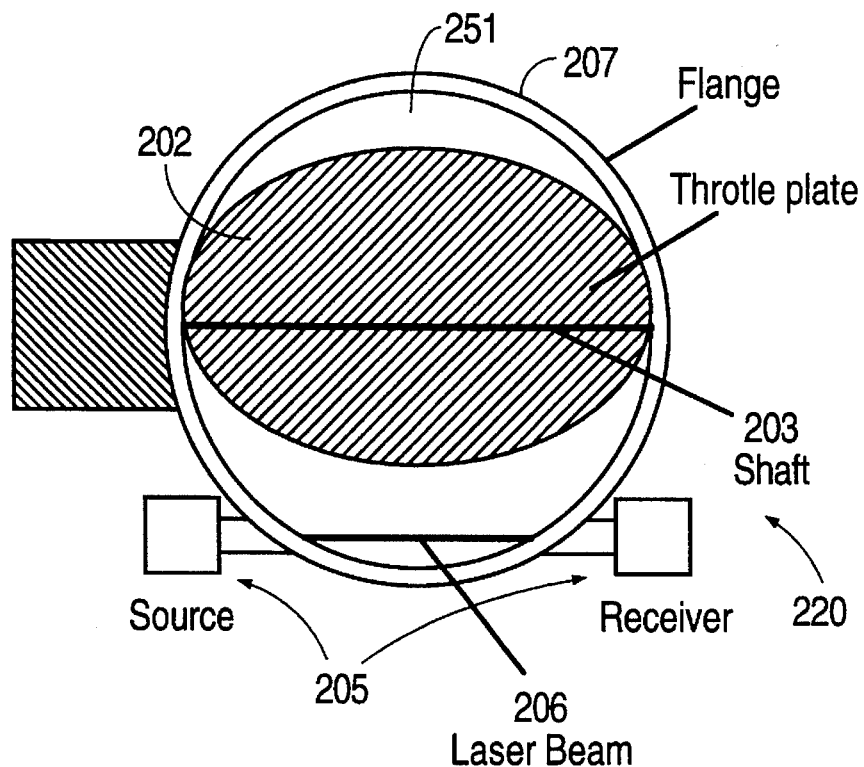
FIG. 2 is a top view of a butterfly valve manifold 220 having a particle sensor 205 installed in accordance with the present invention.

An embodiment of the present invention is illustrated by FIG. 2. In FIG. 2, a laser beam 206 of a particle sensor 205 is projected across a pump line opening 251 parallel to the axis of a butterfly valve 220. Laser beam 206 is displaced from a center line (e.g. the line along drive shaft 203), so that laser beam 206 is in the path of gas flow during normal operation of the plasma etching process in which butterfly valve 220 partially occlude pump line opening 251. Plate 202 of butterfly valve is typically positioned during normal operation to be between 15 to 30 degrees from the cross-section of pump line opening 251.

The placement of particle sensor 205 in the configuration of FIG. 2 for monitoring particles above the pump is not obvious to one of ordinary skill in the particle monitoring art for at least two reasons. First, turbo pumped etch systems generally operate at very low pressures, at which it is generally believed that the gas flow is too light to suspend particles. Thus, conventional wisdom believes that the gas flow is of limited effectiveness in directing particles to a laser beam of a particle monitor. Second, particle sensors are generally recognized to have too low sensitivity for this application because of the interference from the nearby plasma glow in the process chamber.

However, conventional wisdom does not take into account that, at normal operating position of butterfly valve 202, the gas flow through pipe: line opening 251 is actually large enough to suspend the: types of particles frequently present in the process chamber. These particles originate from coatings on the fixtures of the process chamber. Such particles, which each tend to have a large surface area and a relatively small mass, behave typically more like flakes than spheres. Further, in many turbo pump installations, a relatively direct pumping path is typically available without bends, thereby avoiding loss of particles from the low pressure gas flow due to centripetal acceleration at the bends. As a result, even at low pressure (e.g. 5–10 millitorr), sufficient gas flow exists to move such particles to turbo pump 150. At the same time, a typical dimension of these relatively large surface area particles exceeds 0.3 microns ($\mu$m). The combination of these factors allows the present invention to successfully detect particles in a very low pressure gas flow using a convention particle sensor.

Figure 3:
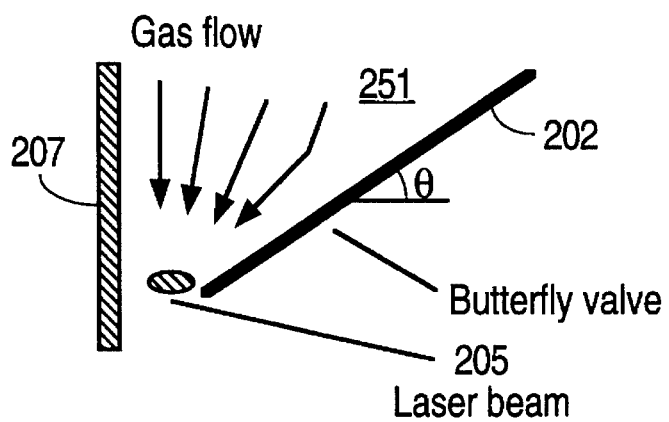
FIG. 3 shows, in the embodiment of FIG. 2, how particle-carrying exhaust gases from process chamber 201 flow through a laser beam 206 of particle sensor 205.

FIG. 3 is a side view of the configuration shown in FIG. 2. Laser beam 206 is positioned so that the gas flow is funneled into turbo pump 150 by virtue of the angled operating position of butterfly valve plate 202. FIG. 3 shows that butterfly valve plate 202 is positioned at an angle θ from a cross-section of weldment 220. The resulting gas flow carries free particles and flows across laser beam 206. The general operating parameters of particle sensor 206 is calculated below.

First, pump line opening 251 has an effective area, i.e. the total area of pump line 251 subtracting the area restricted by butterfly valve weldment 220, given by:

$$A = \pi (d/2)^2 * (1 - \cos \theta)$$

where θ is the diameter of butterfly valve weldment 220 and θ is the positional angle of valve plate 202 (θ=0 represents complete restriction of pump line opening 251). Thus, the gas velocity through the effective area of pump opening 251 is given by $$v = V/A,$$

where V is the volume of gas being pumped and A is the effective area computed above.

Thus, for typical process parameters of 30 mTorr pressure and a gas flow of 150 sccm (standard cubic centimeters per minute) with an angle of 30° for valve plate 202 and the diameter of 6" for weldment 220, the gas velocity is 30 m/sec at narrowest part of pump line opening 251, and 3.5 m/sec at the widest part. In the process chamber, the gas velocity is much lower because the chamber dimensions are considerably larger than those of the butterfly valve 220. For example, if the chamber is 18" in diameter, the mean gas velocity is approximately 10% of that at the pump line opening 251, i.e. approximately 0.35 m/sec. At this combination of low pressure and low velocity, the motion of the particles substantially track that of the gas flow. In FIG. 2, particle sensor 205 is located in or near butterfly valve plate 202. In that embodiment, laser beam 206 is displaced 2.75" from the axis of pump line opening 251 in a 6" diameter weldment. Laser beam 206 projects across the narrow opening through which gas flows during normal operation. A suitable particle sensor for implementing particle sensor 206 is a bright-field or a quasi-bright field particle sensor. One example of such a particle sensor is described in a copending U.S. patent application ("Copending Application"), entitled "Quasi-Bright Field Particle Sensor", by Peter Borden et al, filed on Apr. 1, 1993, Ser. No. 08/041,070, assigned to High Yield Technology, which is also the assignee of the present application. The disclosure of Copending Application is hereby incorporated by reference in its entirety to provide background information of a bright field or a quasi-bright field particle sensor. Such a sensor is relatively immune to plasma glow and has good velocity response. The velocity response of such a sensor is determined by the detector bandwidth and the width of the beam. In the system described in the Copending Application, a long focal length would provide a relatively wide beam which would achieve the velocity response up to the 30 m/sec require.

In particle sensor 205, the actual sensor optics are recessed from weldment 220. A recessed location for sensor optics prevents the optics from being coated by process by-products and also reduces the susceptibility of particle sensor 205 from the noise created by the intensity of plasma glow in the process chamber. In addition, the housing for particle sensor 205 can be heated to further retard deposition of process by-products onto the exposed surfaces of particle sensor 205. Heating of pump lines and pumping systems is a commonly used technique in process equipment to retard deposition by process by-products.

Alternatively, particle sensor 205 can be implemented by a dark-field particle sensor, having pick-up optics placed off-axis (e.g. 90°) from laser beam 205 to collect scattered light. If a dark-field particle sensor is used, the pick-up optics should include a narrow-band optical filter tuned to the wavelength of laser beam 206 to reduce particle sensor 205's susceptibility to the intensity of plasma glow admitted. As in the bright field sensor described in the Copending Application, a dark-field sensor having a wide beam and carefully selector detector bandwidth would achieve the velocity response in this application. Of course, a dark-field sensor has bulkier optical components for collecting the scattered light, which must be accommodated in the available space.

The above detailed description is provided to illustrate the specific embodiments of the present invention is not intended to be limiting. Numerous modifications and variations within the scope of the present invention are possible. The present invention is defined by the following claims.

What is claimed is:

1. A method for monitoring particles in an exhaust line of a process chamber, said exhaust line being equipped with a throttle valve for restricting an opening of said exhaust line, said method comprising the steps of:

positioning a laser beam such that said laser beam crosses an opening created by said throttle valve being partially open said laser beam being positioned offset from a principal axis of said exhaust line; and positioning a detector for detecting particles impinged by said laser beam.

2. A method as in claim 1, wherein said step of positioning a detector uses a detector which is part of a bright-field particle sensor.

3. A method as in claim 1, wherein said step of positioning a detector positions said detector to collect scattered light.

4. A method as in claim 1, wherein said throttle valve is a butterfly valve.

5. A method as in claim 1, wherein said throttle valve is a linear gate valve.

6. A method for monitoring particles in an exhaust line of a process chamber, said exhaust line being equipped with a throttle valve for restricting an opening of said exhaust line, said method comprising the steps of:

positioning a laser beam such that said laser beam crosses an opening created by said throttle valve being partially open;

positioning a detector for detecting particles impinged by said laser beam; and providing a narrow band optical filter for attenuating noise due to plasma in said process chamber.

7. An apparatus for monitoring particles in an exhaust line of a process chamber, said exhaust line being equipped with a throttle valve for restricting an opening of said exhaust line, said apparatus comprising:

a laser beam positioned such that said laser beam crosses an opening created by said throttle valve being partially open, said laser beam being positioned offset from a principal axis of said exhaust line; and a detector positioned for detecting particles impinged by said laser beam.

8. An apparatus as in claim 7, wherein said detector is part of a bright-field particle sensor.

9. An apparatus as in claim 7, wherein said detector is positioned to collect scattered light.

10. An apparatus as in claim 7, wherein said throttle valve is a butterfly valve.

11. An apparatus as in claim 7, wherein said throttle valve is a linear gate valve.

12. An apparatus for monitoring particles in an exhaust line of a process chamber, said exhaust line being equipped with a throttle valve for restricting an opening of said exhaust line, said apparatus comprising:

a laser beam positioned such that said laser beam crosses an opening created by said throttle valve being partially open;

a detector positioned for detecting particles impinged by said laser beam; and a narrow band optical filter for attenuating noise due to plasma in said process chamber.

* * * * *

UNITED STATES PATENT AND TRADEMARK OFFICE
CERTIFICATE OF CORRECTION

PATENT NO.   :   5,534,706
DATED        :   July 9, 1996
INVENTOR(S)  :   Borden, et al.

It is certified that error appears in the above-identified patent and that said Letters Patent is hereby corrected as shown below:

At column 1, line 65, delete "p:Lasma" and insert --plasma--.

At column 4, lines 12 and 13, delete ":".

At column 4, line 44, delete "$\theta$" and insert --d--.

Signed and Sealed this

Twenty-first Day of January, 1997

Attest:

BRUCE LEHMAN

*Attesting Officer*     Commissioner of Patents and Trademarks